United States Patent
Sun et al.

(10) Patent No.: US 8,436,216 B2
(45) Date of Patent: May 7, 2013

(54) PROCESS FOR MAKING 1,1,1,4,4,4-HEXAFLUORO-2-BUTENE

(75) Inventors: Xuehui Sun, Swedesboro, NJ (US); Mario Joseph Nappa, Newark, DE (US); Win-Chung Lee, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 270 days.

(21) Appl. No.: 12/922,858

(22) PCT Filed: Mar. 18, 2009

(86) PCT No.: PCT/US2009/037459
§ 371 (c)(1),
(2), (4) Date: Sep. 16, 2010

(87) PCT Pub. No.: WO2009/117458
PCT Pub. Date: Sep. 24, 2009

(65) Prior Publication Data
US 2011/0028769 A1 Feb. 3, 2011

Related U.S. Application Data

(60) Provisional application No. 61/037,847, filed on Mar. 19, 2008.

(51) Int. Cl.
C07C 21/00 (2006.01)
C07C 17/00 (2006.01)
C22C 9/00 (2006.01)

(52) U.S. Cl.
USPC .................. 570/153; 570/156; 420/469

(58) Field of Classification Search .................. None
See application file for complete search history.

(56) References Cited

U.S. PATENT DOCUMENTS 5,516,951 A  5/1996  Aoyama
5,523,497 A  6/1996  Lui et al.

OTHER PUBLICATIONS

Adams D. J. et. al.: "Towards the Synthesis of Perfluoroalkylated Derivates of Xantphos", Tetrahedron, Elsevier Science Publishers, Amsterdam, NL, vol. 60, No. 18, Apr. 26, 2004, pp. 4079-4085, XP004502641. ISSN: 004-4020, Scheme 2; chapter 4.1.3 and 4.1.6; pages.
J. Org. Chem. 1997, vol. 62, No. 6, pp. 1576-1577. 1,1-Bis(dimethylamino)-2.2.2-trifluoroethane, a Readily-Available Precursor to the Novel Fluorinated Building Bl9ock 1, 1-Bis(dimethylamino)-2,2-difluoroethene, Yuelian Xu, William R. Dolbier, Jr., and Xiao X. Rong.
PCTUS2009/037459 International Search Report, Mar. 19, 2008.

*Primary Examiner* — Sudhakar Katakam
*Assistant Examiner* — Clinton Brooks

(57) ABSTRACT

A process is disclosed for making 1,1,1,4,4,4-hexafluoro-2-butene. The process involves reacting 2,2-dichloro-1,1,1-trifluoroethane with copper in the presence of an amide solvent and 2,2'-bipyridine. A process is also disclosed for making 1,1,1,4,4,4-hexafluoro-2-butene. The process involves reacting 2,2-dichloro-1,1,1-trifluoroethane with copper in the presence of an amide solvent and a Cu(I) salt. A process is further disclosed for making 1,1,1,4,4,4-hexafluoro-2-butene. The process involves reacting 2,2-dichloro-1,1,1-trifluoroethane with copper in the presence of an amide solvent, 2,2'-bipyridine and a Cu(I) salt.

9 Claims, No Drawings

PROCESS FOR MAKING 1,1,1,4,4,4-HEXAFLUORO-2-BUTENE

BACKGROUND

1. Field of the Disclosure

The present disclosure relates to a production of 1,1,1,4,4,4-hexafluoro-2-butene by using 2,2-dichloro-1,1,1-trifluoroethane and copper.

2. Description of Related Art

The fluorocarbon industry has been working for the past few decades to find replacement refrigerants and foam expansion agents for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as foam expansion agents, refrigerants, solvents, fire extinguishing agents and propellants. These new compounds, such as HFC-245fa (1,1,1,3,3-pentafluoropropane), have zero ozone depletion potential and thus are not affected by the current regulatory phase-out as a result of the Montreal Protocol.

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for compositions that meet both low ozone depletion standards as well as having low global warming potentials. Certain hydrofluoroolefins, such as 1,1,1,4,4,4-hexafluoro-2-butene (F11E), are believed to meet both goals.

In U.S. Pat. No. 5,516,951, Aoyama disclosed a process for making F11E by reacting 2,2-dichloro-1,1,1-trifluoroethane (HCFC-123) with copper and an amine. However, the yield is low. According to the results reported by Xu, et al. in J. Org. Chem. 1997, 62, 1576-1577, such processes generate $CF_3CH_2Cl$ byproduct which is hard to separate and other impurities.

BRIEF SUMMARY OF THE DISCLOSURE

A process has been provided to make F11E. The process comprises reacting HCFC-123 with copper in the presence of an amide solvent and 2,2'-bipyridine.

A process has also been provided to make F11E. The process comprises reacting HCFC-123 with copper in the presence of an amide solvent and a Cu(I) salt.

A process has further been provided to make F11E. The process comprises reacting HCFC-123 with copper in the presence of an amide solvent, 2,2'-bipyridine and a Cu(I) salt.

The foregoing general description and the following detailed description are exemplary and explanatory only and are not restrictive of the invention as defined in the appended claims.

DETAILED DESCRIPTION

Before addressing details of embodiments described below, some terms are defined or clarified.

F11E may exist as one of two configurational isomers, E or Z. F11E as used herein refers to the isomers, E-F11E or Z-F11E, as well as any combinations or mixtures of such isomers.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Realizing the need for processes that provide high yield and/or high selectivity of making F11E, inventors provide here a process to make F11E. The process comprises reacting HCFC-123 with copper in the presence of an amide solvent and 2,2'-bipyridine.

HCFC-123 is commercially available from E. I. du Pont de Nemours and Company incorporated in Delaware.

Copper used herein is metal copper having zero valence. In one embodiment of this invention, copper powder is used for the reaction.

Typical amide solvents used herein include dimethylformamide (DMF), dimethylacetamide, N-methylpyrrolidone, et al. In one embodiment of this invention, the amide solvent is DMF.

Another process has also been provided to make F11E. The process comprises reacting HCFC-123 with copper in the presence of an amide solvent and a Cu(I) salt.

Typical Cu(I) salts used herein include CuCl, CuBr, CuI, copper(I) acetate, et al. In one embodiment of this invention, the Cu(I) salt is CuCl.

Optionally, an amine can also be present in the reaction mixture. Typically such amines include secondary amines such as dimethylamine, diethylamine, di-n-propylamine, diisopropylamine, di-n-butylamine, et al.; tertiary amines such as trimethylamine, triethylamine, tri-n-propylamine, triisopropylamine, tri-n-butylamine, et al.; cyclic amines such as morpholine, piperazine, piperidine, pyrrolidine, et al.

A process has further been provided to make F11E. The process comprises reacting HCFC-123 with copper in the presence of an amide solvent, 2,2'-bipyridine and a Cu(I) salt.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

The temperature employed in the reaction process typically ranges from about 20° C. to about 150° C. In one embodiment of the invention, the temperature employed in the reaction process ranges from about 60° C. to about 150° C.

Reaction time is not critical and typically ranges from about 0.5 hour to about 10 hours.

The pressure employed in the reaction is not critical. Typically, the reaction is conducted under autogenous pressure.

EXAMPLES

The concepts described herein will be further described in the following examples, which do not limit the scope of the invention described in the claims.

Example 1

Example 1 demonstrates the reactions in the presence of 2,2'-bipyridine, CuCl and DMF.

At room temperature, a 80 ml Fisher Porter tube was charged with 1.85 g (0.029 mol) of Cu powder, 2 g (0.013 mol) of HCFC-123, 0.15 g (0.0015 mol) of CuCl, 0.3 g (0.0019 mol) of 2,2'-bipyridine and 10 ml of DMF. The tube was purged with $N_2$ for 5 minutes and then was sealed. The reaction mixture was stirred at 80° C. for 4 hours. The pressure of the tube increased to 10.5 psig at 80° C. It dropped to 4.5 psig after the tube was cooled down to room temperature. At the end of the reaction, both vapor phase and liquid phase of the product mixture in the tube were analyzed by GC-MS. The analytical results were given in units of GC area % in Table 1 and Table 2 below. Small amounts of byproducts having GC area % less than 0.05 were not included in the Tables.

TABLE 1

| (vapor phase) | | | |
| --- | --- | --- | --- |
| E-F11E | Z-F11E | $CF_3CH=CHCF_2Cl$ | HCFC-123 |
| 82.62 | 13.93 | 0.18 | 3.23 |

TABLE 2

| (liquid phase) | | | | |
| --- | --- | --- | --- | --- |
| E-F11E | Z-F11E | $CF_3CH=CHCF_2Cl$ | HCFC-123 | unknowns |
| 46.88 | 49.71 | 0.65 | 2.40 | 0.33 |

Example 2

Example 2 demonstrates the reactions in the presence of CuCl and DMF.

At room temperature, a 80 ml Fisher Porter tube was charged with 4 g (0.063 mol) of Cu powder, 2 g (0.013 mol) of HCFC-123, 0.15 g (0.0015 mol) of CuCl and 10 ml of DMF. The tube was purged with $N_2$ for 5 minutes and then was sealed. The reaction mixture was stirred at 90° C. for 6 hours. The pressure of the tube increased to 10 psig at 90° C. It dropped to 4 psig after the tube was cooled down to room temperature. At the end of the reaction, both vapor phase and liquid phase of the product mixture in the tube were analyzed by GC-MS. The analytical results were given in units of GC area % in Table 3 and Table 4 below. Small amounts of byproducts having GC area % less than 0.05 were not included in the Tables.

TABLE 3

| (vapor phase) | | | |
| --- | --- | --- | --- |
| E-F11E | Z-F11E | $CF_3CH=CHCF_2Cl$ | HCFC-123 |
| 60.84 | 10.27 | 0.09 | 20.80 |

TABLE 4

| (liquid phase) | | | | |
| --- | --- | --- | --- | --- |
| E-F11E | Z-F11E | $CF_3CH=CHCF_2Cl$ | HCFC-123 | unknowns |
| 15.31 | 16.21 | 0.10 | 68.19 | 0.19 |

Example 3

Example 3 demonstrates the reactions in the presence of 2,2'-bipyridine and DMF.

At room temperature, a 80 ml Fisher Porter tube was charged with 3.9 g (0.06 mol) of Cu powder, 4 g (0.026 mol) of HCFC-123, 0.3 g (0.0019 mol) of 2,2-bipyridine and 10 ml of DMF. The tube was purged with $N_2$ for 5 minutes and then was sealed. The reaction mixture was stirred at 80° C. for 4 hours. The pressure of the tube increased to 15.5 psig at 80° C. It dropped to 5.5 psig after the tube was cooled down to room temperature. At the end of the reaction, both vapor phase and liquid phase of the product mixture in the tube were analyzed by GC-MS. The analytical results were given in units of GC area % in Table 5 and Table 6 below. Small amounts of byproducts having GC area % less than 0.05 were not included in the Tables.

TABLE 5

| (vapor phase) | | | | | |
| --- | --- | --- | --- | --- | --- |
| E-F11E | Z-F11E | $CF_3CH_2CF_3$ | $CF_3CH=CHCF_2Cl$ | HCFC-123 | |
| 81.79 | 13.67 | 0.13 | 0.16 | 4.21 | |

TABLE 6

| (liquid phase) | | | | | |
| --- | --- | --- | --- | --- | --- |
| E-F11E | Z-F11E | $CF_3CH_2CF_3$ | $CF_3CH=CHCF_2Cl$ | HCFC-123 | unknowns |
| 44.44 | 45.69 | 0.15 | 0.36 | 8.88 | 0.46 |

Example 4

Example 4 demonstrates the reactions in the presence of di-n-butylamine, CuCl and DMF.

At room temperature, a 80 ml Fisher Porter tube was charged with 1.85 g (0.029 mol) of Cu powder, 2 g (0.013 mol) of HCFC-123, 0.15 g (0.0015 mol) of CuCl, 3 g (0.023 mol) of di-n-butylamine and 10 ml of DMF. The tube was purged with $N_2$ for 5 minutes and then was sealed. The reaction mixture was stirred at 80° C. for 6 hours. The pressure of the tube increased to 10 psig at 80° C. It dropped to 4 psig after the tube was cooled down to room temperature. At the end of the reaction, both vapor phase and liquid phase of the product mixture in the tube were analyzed by GC-MS. The analytical results were given in units of GC area % in Table 7 and Table 8 below. Small amounts of byproducts having GC area % less than 0.05 were not included in the Tables.

TABLE 7

| (vapor phase) | |
|---|---|
| $CF_2=CH_2$ | 1.77 |
| $CF_3CH_3$ | 0.07 |
| $CF_3CH_2CF_3$ | 0.16 |
| $CF_3CH_2Cl$ | 1.01 |
| E-F11E | 77.73 |
| Z-F11E | 12.77 |
| $CF_3CH=CHCF_2Cl$ | 0.21 |
| HCFC-123 | 3.47 |
| unknowns | 2.68 |

TABLE 8

| (liquid phase) | |
|---|---|
| $CF_3CH_2CF_3$ | 0.21 |
| $CF_3CH_2Cl$ | 3.10 |
| E-F11E | 34.07 |
| Z-F11E | 41.26 |
| $CF_3CH=CHCF_2Cl$ | 0.51 |
| $CF_3CH=CHCF_2H$ | 0.47 |
| HCFC-123 | 13.99 |
| unknowns | 6.39 |

Example 5

Comparative

Example 5 demonstrates the reactions in the presence of di-n-butylamine and CuCl.

At room temperature, a 80 ml Fisher Porter tube was charged with 1.85 g (0.029 mol) of Cu powder, 2 g (0.013 mol) of HCFC-123, 0.2 g (0.002 mol) of CuCl and 10 g (0.08 mol) of di-n-butylamine. The tube was purged with $N_2$ for 5 minutes and then was sealed. The reaction mixture was stirred at 40-80° C. for 6.5 hours. The pressure of the tube increased to 11 psig at 80° C. It dropped to 4 psig after the tube was cooled down to room temperature. Reaction mixture also turned to solid upon cooling. 10 ml of DMF was added into the solid and about half amount of the solid materials dissolved. Both vapor phase and liquid phase of the product mixture in the tube were analyzed by GC-MS. The analytical results were given in units of GC area % in Table 9 and Table 10 below. Small amounts of byproducts having GC area % less than 0.05 were not included in the Tables.

TABLE 9

| (vapor phase) | |
|---|---|
| $CF_2=CH_2$ | 5.53 |
| $CF_3CH_3$ | 0.07 |
| $CF_3CH_2Cl$ | 1.29 |
| $C_4H_2F_4$ | 0.48 |

TABLE 9-continued

| (vapor phase) | |
|---|---|
| $CF_3(CH_3)C=CF_2$ | 1.05 |
| E-F11E | 76.73 |
| Z-F11E | 11.82 |
| $CF_3CH=CHCF_2H$ | 0.49 |
| HCFC-123 | 0.14 |
| unknowns | 2.63 |

TABLE 10

| (liquid phase) | |
|---|---|
| $CF_3(CH_3)C=CF_2$ | 0.92 |
| E-F11E | 35.71 |
| $C_4H_2F_4$ | 0.27 |
| Z-F11E | 36.15 |
| $CF_3CH=CHCF_2H$ | 1.77 |
| HCFC-123 | 2.43 |
| $CF_3CH=NC_4H_9$ | 14.26 |
| unknowns | 11.10 |

Example 6

Comparative

Example 6 demonstrates the reactions in the presence of diethylamine.

At room temperature, a 80 ml Fisher Porter tube was charged with 1.85 g (0.029 mol) of Cu powder, 2 g (0.013 mol) of HCFC-123 and 3 g (0.04 mol) of diethylamine. The tube was purged with $N_2$ for 5 minutes and then was sealed. The reaction mixture was stirred at room temperature for 64 hours. The pressure of the tube increased to 5 psig from 3 psig. Reaction mixture turned into a solid at end. 10 ml of DMF was added into the solid and about half amount of the solid materials dissolved. Both vapor phase and liquid phase of the product mixture in the tube were analyzed by GC-MS. The analytical results were given in units of GC area % in Table 11 and Table 12 below. Small amounts of byproducts having GC area % less than 0.05 were not included in the Tables.

TABLE 11

| (vapor phase) | |
|---|---|
| $CF_2=CH_2$ | 8.60 |
| $CF_3CH_2Cl$ | 0.56 |
| $C_4H_2F_4$ | 1.74 |
| $CF_3(CH_3)C=CF_2$ | 5.11 |
| E-F11E | 65.26 |
| Z-F11E | 10.25 |
| $CF_3CH=CHCF_2H$ | 1.58 |
| HCFC-123 | 2.73 |
| $CF_3CH=CHCF_2Cl$ | 1.58 |
| unknowns | 3.85 |

TABLE 12

| (liquid phase) | |
|---|---|
| $CF_3(CH_3)C=CF_2$ | 1.92 |
| E-F11E | 8.92 |
| $CF_3CH_2Cl$ | 0.75 |
| $C_4H_2F_4$ | 0.19 |
| Z-F11E | 26.23 |

TABLE 12-continued (liquid phase)

| | |
|---|---|
| $CF_3CH=CHCF_2H$ | 4.91 |
| HCFC-123 | 10.63 |
| unknowns | 46.46 |

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for making 1,1,1,4,4,4-hexafluoro-2-butene comprising reacting 2,2-dichloro-1,1,1-trifluoroethane with copper in the presence of an amide solvent and 2,2'-bipyridine.

2. The process of claim 1, wherein the reaction also takes place in the presence of a Cu(I) salt.

3. The process of claim 1 wherein said amide solvent is selected from the group consisting of dimethylformamide, dimethylacetamide and N-methylpyrrolidone.

4. The process of claim 3 wherein said amide solvent is dimethylformamide.

5. The process of claim 2 wherein said Cu(I) salt is selected from the group consisting of CuCl, CuBr, CuI and copper(I) acetate.

6. The process of claim 5 wherein said Cu(I) salt is CuCl.

7. The process of claim 1 wherein said process is conducted in the presence of an amine.

8. The process of claim 1 wherein said process is conducted at a temperature of from about 20° C. to about 150° C.

9. The process of claim 8 wherein said temperature is from about 60° C. to about 150° C.

* * * * *